United States Patent
Cervone et al.

(10) Patent No.: US 8,637,734 B2
(45) Date of Patent: Jan. 28, 2014

(54) USE OF PLANTS WITH REDUCED LEVELS OF DE-ESTERIFIED HOMOGALACTURONAN IN THE CELL WALL OR PORTIONS THEREOF FOR IMPROVING THE SACCHARIFICATION OF PLANT BIOMASSES

(75) Inventors: Felice Cervone, Rome (IT); Giulia De Lorenzo, Rome (IT); Daniela Bellincampi, Rome (IT); Simone Ferrari, Rome (IT); Vincenzo Lionetti, Rome (IT); Giovanni Salvi, Rome (IT); Fedra Francocci, Rome (IT); Daniela Pontiggia, Rome (IT)

(73) Assignee: Universita' degli Studi di Roma "La Sapienza", Rome (IT)

( * ) Notice: Subject to any disclaimer, the term of this patent is extended or adjusted under 35 U.S.C. 154(b) by 456 days.

(21) Appl. No.: 12/648,644

(22) Filed: Dec. 29, 2009

(65) Prior Publication Data
US 2010/0170008 A1    Jul. 1, 2010

(30) Foreign Application Priority Data
Dec. 30, 2008 (IT) .............................. RM2008A0696

(51) Int. Cl.
*C12N 15/82* (2006.01)
*C12N 15/10* (2006.01)
*C12N 15/00* (2006.01)
*C07H 21/04* (2006.01)

(52) U.S. Cl.
USPC ........... 800/284; 800/278; 800/295; 800/298; 435/320.1; 435/468; 536/23.1

(58) Field of Classification Search
None
See application file for complete search history.

(56) References Cited

U.S. PATENT DOCUMENTS

2005/0233423 A1* 10/2005 Berka et al. ................... 435/101
2007/0250961 A1* 10/2007 Blaylock et al. .............. 800/283

FOREIGN PATENT DOCUMENTS

| EP | 09180685.1 | 7/2010 |
| IT | RM20110588 | 5/2013 |
| WO | 2005005470 | 1/2005 |
| WO | 2006068603 | 6/2006 |

OTHER PUBLICATIONS

Bartling et al 1995 Microbiology 141:873-881 Sequence alignment provided in body of office action.*
Carpodicasa, Cristina et al., Targeted Modification of Homogalacturonan by Transgenic Expression of a Fungal Polygalacturonase Alters Plant Growth, Plant Physiology, Jul. 2004, pp. 1294-1305, vol. 135.
Cervone, Felice, Improving Degradation of Biomass by Improving Cell Wall Digestibility, Universita di Roma "Sapienza", Jun. 2008 (XP002532193).
Lionetti, Vincenzo et al., Overexpression of Pectin Methylesterase Inhibitors in *Arabidopsis* Restricts Fungal Infenction by *Botrytis cinerea*, Plant Physiology, Apr. 2007, pp. 1871-1880, vol. 143.
Nardini, Andrea et al., Reduced Content of Homogalacturonan Does Not Alter the Ion-Mediated Increase in Xylem Hydraulic Conductivity in Tobacco, Plant Physiology, Apr. 2007, pp. 1975-19681, vol. 143.
European Research Council, Project Database: CORDIS, "Grantees & Projects", 2007-2008 (XP002532194).

* cited by examiner

*Primary Examiner* — Brent T Page
(74) *Attorney, Agent, or Firm* — Lucas & Mercanti, LLP

(57) ABSTRACT

The present invention relates to expression in plants of pectinolytic enzymes and of pectin methylesterase inhibitors for increasing the degradability of plant tissues through enzymatic digestion, thus improving saccharification efficiency.

4 Claims, 3 Drawing Sheets

Figure 1:
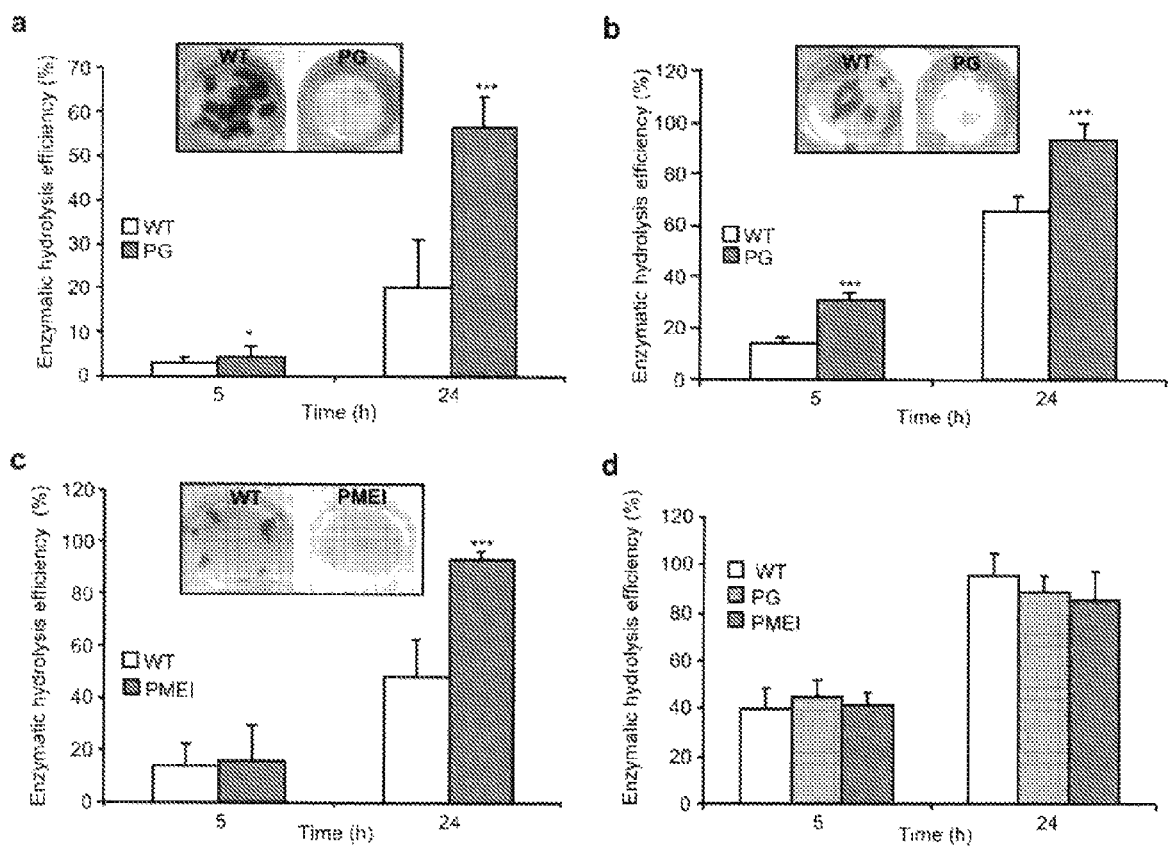

SEQUENCE LISTING

<160> NUMBER OF SEQ ID NOS: 6

<210> SEQ ID NO 1
<211> LENGTH: 1005
<212> TYPE: DNA
<213> ORGANISM: Aspergillus niger

<400> SEQUENCE: 1

```
gacagctgca cgttcaccgc tgccgctgct aaagcgggca aggcgaaatg ctctactatc      60
acccttaaca acatcgaagt tccagctgga accaccctcg acctgaccgg tctcaccagc     120
ggtaccaagg tcatcttcga gggcaccacg accttccagt acgaagaatg ggcaggcccc     180
ttgatctcca tgagtggcga acatatcacc gtcactggtg cctccggcca cctcatcaat     240
tgcgatggtc cgcgctggtg ggatggcaag ggaaccagcg gaaagaagaa gcccaagttc     300
ttttacgccc atggccttga ctcctcgtct attactggat taaacatcaa aaacaccccc     360
cttatggcgt ttagtgtcca ggcgaatgac attacgttta ccgatgttac catcaataat     420
gcggatggcg acacccaggg tggacacgac actgatgcgt cgatgttgg  caactcggtc     480
ggggtgaata tcattaagcc ttgggtccat aaccaggatg actgtcttgc ggttaactct     540
ggcgagaaca tctggttcac cggcggcacc tgcattggcg gccacggtct ctccatcggc     600
tctgtcggcg accgctccaa caacgtcgtc aagaacgtca ccatcgaaca ctccaccgtg     660
agcaattccg aaaacgccgt ccgaattaag accatctctg gcgccactgg ctccgtgtcc     720
gagattacgt actccaacat cgtcatgtct ggcatctccg attacggcgt ggtcattcag     780
caggattacg aagacggcaa gcctacgggt aagccgacga acgtgtcac  tattcaggat     840
gttaagctgg agagcgtgac tggtagcgtg gatagtgggg ctactgagat ctatcttctt     900
tgcgggtctg gtagctgctc ggactggacc tgggacgatg tgaaagttac cggggggaag     960
aagtccaccg cttgcaagaa cttcccttcg gtggcctctt gttag               1005
```

<210> SEQ ID NO 2
<211> LENGTH: 334
<212> TYPE: PRT
<213> ORGANISM: Aspergillus niger

<400> SEQUENCE: 2

Asp Ser Cys Thr Phe Thr Ala Ala Ala Lys Ala Gly Lys Ala Lys
1               5                   10                  15

Cys Ser Thr Ile Thr Leu Asn Asn Ile Glu Val Pro Ala Gly Thr Thr
            20                  25                  30

Leu Asp Leu Thr Gly Leu Thr Ser Gly Thr Lys Val Ile Phe Glu Gly
        35                  40                  45

Thr Thr Thr Phe Gln Tyr Glu Glu Trp Ala Gly Pro Leu Ile Ser Met
50                  55                  60

Ser Gly Glu His Ile Thr Val Thr Gly Ala Ser Gly His Leu Ile Asn
65                  70                  75                  80

Cys Asp Gly Ala Arg Trp Trp Asp Gly Lys Gly Thr Ser Gly Lys Lys
                85                  90                  95

Lys Pro Lys Phe Phe Tyr Ala His Gly Leu Asp Ser Ser Ile Thr
            100                 105                 110

Gly Leu Asn Ile Lys Asn Thr Pro Leu Met Ala Phe Ser Val Gln Ala
        115                 120                 125

Asn Asp Ile Thr Phe Thr Asp Val Thr Ile Asn Asn Ala Asp Gly Asp
130                 135                 140

Thr Gln Gly Gly His Asp Thr Asp Ala Phe Asp Val Gly Asn Ser Val
145                 150                 155                 160

Gly Val Asn Ile Ile Lys Pro Trp Val His Asn Gln Asp Asp Cys Leu
                165                 170                 175

Ala Val Asn Ser Gly Glu Asn Ile Trp Phe Thr Gly Gly Thr Cys Ile
            180                 185                 190

Gly Gly His Gly Leu Ser Ile Gly Ser Val Gly Asp Arg Ser Asn Asn
        195                 200                 205

Val Val Lys Asn Val Thr Ile Glu His Ser Thr Val Ser Asn Ser Glu
210                 215                 220

Asn Ala Val Arg Ile Lys Thr Ile Ser Gly Ala Thr Gly Ser Val Ser
225                 230                 235                 240

Glu Ile Thr Tyr Ser Asn Ile Val Met Ser Gly Ile Ser Asp Tyr Gly
                245                 250                 255

Val Val Ile Gln Gln Asp Tyr Glu Asp Gly Lys Pro Thr Gly Lys Pro
            260                 265                 270

Thr Asn Gly Val Thr Ile Gln Asp Val Lys Leu Glu Ser Val Thr Gly
        275                 280                 285

Ser Val Asp Ser Gly Ala Thr Glu Ile Tyr Leu Leu Cys Gly Ser Gly
290                 295                 300

Ser Cys Ser Asp Trp Thr Trp Asp Asp Val Lys Val Thr Gly Gly Lys
305                 310                 315                 320

Lys Ser Thr Ala Cys Lys Asn Phe Pro Ser Val Ala Ser Cys
                325                 330

<210> SEQ ID NO 3
<211> LENGTH: 522
<212> TYPE: DNA
<213> ORGANISM: Arabidopsis thaliana

<400> SEQUENCE: 3
atggcagcat acctgacgaa cagagtttta atgtcttctc tgatgttttt tgtaatgact    60
ggttctttga acgcacaagt ggcagacata aaagcgatat gtggaaaagc gaaaaaccaa   120
tccttctgta cgagctacat gaaatccaac ccaaagacct caggtgctga tcttcaaacg   180

```
cttgcaaata tcacatttgg ttctgcacaa acaagtgcat cagaaggttt caggaaaatt    240
caatctctag tcaagacagc aaccaacccc actatgaaga aagcatacac ctcatgtgta    300
caacattata agagtgcaat aagcagtctc aatgatgcta agcagagcct ggcgtcaggc    360
gatggcaaag ggttgaacat taaggtttca gcagctatgg aaggaccttc aacatgtgaa    420
caagacatgg cggatttcaa agttgatcct tcagctgtga agaacagtgg tgattttcag    480
aatatttgtg gcattgtact tgtcatctca aacatgatgt ga                      522

<210> SEQ ID NO 4
<211> LENGTH: 173
<212> TYPE: PRT
<213> ORGANISM: Arabidopsis thaliana

<400> SEQUENCE: 4

Met Ala Ala Tyr Leu Thr Asn Arg Val Leu Met Ser Ser Leu Met Phe
1               5                   10                  15

Phe Val Met Thr Gly Ser Leu Asn Ala Gln Val Ala Asp Ile Lys Ala
            20                  25                  30

Ile Cys Gly Lys Ala Lys Asn Gln Ser Phe Cys Thr Ser Tyr Met Lys
        35                  40                  45

Ser Asn Pro Lys Thr Ser Gly Ala Asp Leu Gln Thr Leu Ala Asn Ile
    50                  55                  60

Thr Phe Gly Ser Ala Gln Thr Ser Ala Ser Glu Gly Phe Arg Lys Ile
65                  70                  75                  80

Gln Ser Leu Val Lys Thr Ala Thr Asn Pro Thr Met Lys Lys Ala Tyr
                85                  90                  95

Thr Ser Cys Val Gln His Tyr Lys Ser Ala Ile Ser Ser Leu Asn Asp
            100                 105                 110

Ala Lys Gln Ser Leu Ala Ser Gly Asp Gly Lys Gly Leu Asn Ile Lys
        115                 120                 125

Val Ser Ala Ala Met Glu Gly Pro Ser Thr Cys Glu Gln Asp Met Ala
    130                 135                 140

Asp Phe Lys Val Asp Pro Ser Ala Val Lys Asn Ser Gly Asp Phe Gln
145                 150                 155                 160

Asn Ile Cys Gly Ile Val Leu Val Ile Ser Asn Met Met
                165                 170

<210> SEQ ID NO 5
<211> LENGTH: 7480
<212> TYPE: DNA
<213> ORGANISM: Erwinia carotovora

<400> SEQUENCE: 5
cccgggggat ctcaaagcaa tcgggtagcg atgctgaatc aataatgagc gaatgatagc     60
gggtgaccgt caaaggctga gctagccctg cgaaaacccc cgtttcgctg tgcgcaatct    120
cagaggtttt cccgtgcatg acctgccgtg ctcgcaccac acgcgcgccg aacgcctgtc    180
ccatcgcctg atggccaaga cacacgccca gaataggcag tttatcggca aagtgacgga    240
tagcagccag tgaaatgccc gcctcatccg gcgtacaagg gccaggtgaa ttaaccaatc    300
gctcaggggc aagccgttca atctcgcgca gcgtcagttc atcattacgc ttcaccacga    360
cctgtgcgcc aagctcgcaa aagtattggt aaaggttgta ggtaaaggag tcgtagttat    420
cgataattag cagcatagtc attgcactgt tagtcggaaa agccgtacta acatacatga    480
aatccgcgtc aggtacccac ccctcgtcac catcaaagac aaaggtggcg atctcgctgt    540
ttaagaaatt agcatggtaa taattttatc gatcataaat catttatttc atcagtaaac    600
```

```
atctttatta ataggcctta tttattatcc caattcacag taaacgatta ccttgaaatt    660 attttttaaca aaaaaaataa taagaaaaaa ccgcctatga attaattcat tttttttaaa   720
aggaagaaaa actaagggga tcatttctta cgtgatattt tttggtggcg atcacaatcg    780
ttcaacaagc gaataaccac gcatataaac gggataaaaa ataagaacc cttaaaaaca     840 taaagacatg aatttaaatg atttaaatag aaattggttt ctatttgaaa tagatagaca    900
caaatcctct caactgtcct ctgttattta attaatatat ttaacgcccc atcctgtatt    960
gtttgttttt ctggtaacac ttatctcggc tttatagaca aaccttattt tcattttttgt  1020 tgaaacagcc tttttaaatt acacagggtg tgtagtgata aatacccaaa aaattctatg    1080
tcaaggagag tacataatga aatacctact gccttctgca gcagctgggc tggtgctgct    1140
cgctgcccaa ccgacaatgg cggcaaatac ggggggttat gccaccactg acggcggcga    1200
cgtttctggt gcggtgaaaa aaacggcgcg ttctctgcaa gagatcgtcg atatcattga    1260
agccgcgaaa aaggactcaa gcggtaaagc ggtcaaaggc ggagcctacc cgctcgttat    1320
tacctacaac ggtaatgaag atgcgctaat caaagccgcc gaagctaaca tctgcggcca    1380
gtggagcaaa gatccgcgcg tgtgggaaat caaagagttc accaaaggga tcaccattct    1440
cggaaccaac ggttcttccg ctaacttcgg tatctggatg gttaactctt ccaacgttat    1500
cgtacgtaac atgcgcttcg gctatatgcc gggcggtgca aaagatggtg atgccatccg    1560
tatcgataat tcaccgaacg tctggatcga ccacaacgag atcttcgcca agaacttcga    1620
atgtgccggt acgccagaca acgacaccac ctttgaatcc gcggttgata tcaagaaagc    1680
ctcaaccaac gtcaccgtgt cgtacaacta tatccatggc gtgaaaaagg tagggttgag    1740
cggttcaagc aacacggata ccggtcgtaa cctgacttac catcacaata tttacagcga    1800
tgttaactca cgtctgccgc tgcaacgtgg tggccaagtc catgcttata caacctgta    1860 tggcggcatc aaaagttcag gctttaacgt ccgtcagaaa gggatcgcac tgatcgaaag    1920
taactggttc gaaaatgcgc tcaacccagt gaccgcacgt aatgacgatt ccaacttcgg    1980
tacttgggaa ctccgtaaca acaacattac cagcccatct gattttgcta aatacaacat    2040
cacctggggt aaaccatcca caccgcacat caatgcggat gactggaaga gcaccggtaa    2100
attcccagcc gtcccatata gctactctcc agtttctgca cagtgcgtga aggataaact    2160
ggcaagctac gctggcgtag gtaaaaacca ggcagtactg acagcagcca actgtaaata    2220
aacgcgttaa gcccgacgca ttcgttctgc gtcgggttct tcctgagcga gtgcttcggc    2280
ctcgctcatt tttgaaaggc cggagcaaga ttgtcagcgt gaccgccatg aaaatagacg    2340
tcgtactcat gacaatttca ccaataagcc gaggtctatt tttctttat cacgtaaaga    2400 aacgccatat agcgattaat aatcgttatt tcttaaaaaa actaaaattc gcgataaaac    2460
tgactcatca cgcgaacaat attgaatacg tctgtgatag tatattttga cttaaggtag    2520
tgttttacgt tgacggcagc gatcgccaca agaaaaataa caatttaaaa accagccaat    2580
aaagaaactc gagtgcattt attatctact aaaaaagtaa ccttatgatt taccgttact    2640
ttaaagggaa attattttct ataaaaaata aaaccatcca atcatcagta ttaccaaatg    2700
tttcatccgc aatacattta acatttcacc cttggactga tcttattttt tgaccacact    2760 cccctttggtt tttcaccaaa attgaaattc attttttgttg aaaaatttac acttgttaca    2820
tcgggcatag ggatcgataa atgcccatga aaattctatt ccaaggagac agtgataatg    2880 aaataccctat tgcctacggc agccgctgga ttgctattac tcgcggctca acccgcaatg    2940
gccgcaaata cgggcggcta tgccactacg gatggtggag aagtgtccgg tgccgtgaaa    3000
```

```
aaaacggcac gttccatgaa agaaattgtg gatattattg aagccgcgca agtggattca   3060
aaaggcaaga aagtcaaagg cggtgcttac ccgctcatca tcacctatag cggtaatgaa   3120
gactcattaa tcaaagcggc tgaaaagaat atctgcggcc agtggagtaa agacgcacgc   3180
ggcgtacaaa tcaaagagtt caccaaaggc attactatcc agggcaccaa tggctcatcc   3240
gccaacttcg gtgtctggat tgtgaactct tctaatgtcg tgctacgtaa tatccgcttt   3300
ggctatatcc cgggcggcgc gcaacacggc gatgccattc gtatcgataa ctccccgaac   3360
gtctggatcg accacaacga aatctttgcc aagaactttg agtgtaaagg cacgccagac   3420
aatgacacca cctttgaatc ggctgtcgat atcaaaaaag ggtcaactaa cgtcacggta   3480
tcctacaact atattcatgg tatcaagaaa gtcggcctga gcggcgcaag caatacggat   3540
acgggccgta acctgactta ccatcacaat atttatagcg atgttaactc acgcctgccg   3600
ctgcaacgtg gtggtctggt tcacgcgtac aacaacctgt atgacggcat caccggttca   3660
ggctttaatg tgcgtcagaa agggatcgca ctgattgaaa gcaactggtt cgagaatgcg   3720
ctcaacccag tgacagcacg taacgacagc tcaaactttg gtacctggga gctgcgtaac   3780
aacaacatca cgaaaccggc agacttctcc aaatacaaaa tcacctgggg caagccttcc   3840
tctcctcaca tcaatgcgga tgactggaag agcaccggta agttccctgc cgtctcctat   3900
aagtacactc cagtttctgc acagtgcgtg aaggataaac tggcaaacta tgctggcgtc   3960
ggtaaaaacc tggcagtact gacagcagct aactgcaaat aaacgcggtc aggctttctc   4020
cgtcgtcgca agacaggaag caataagtct gaatatcccg cgccgtgact cttcatacag   4080
aagcatggtt ctacccaagc gagcctctta gagctcgctc atttttttat ggaaactcag   4140
gcgcgaacat ggatatgcat tcctaaagag caggcataaa ttaaatatca ggctaattat   4200
taatataatg aattaatagc ttgatttatt aatggagaaa accatccttt aattaatgat   4260
taatcaatag aaataacaac agcccatcaa cacgtgatta ttaataatt tgatcggcat   4320
caactatttc tgacgccatc atctcagcga gtaataaaac gaaatataat tttatttttc   4380
ataaaactct caatggccta attttagaaa aaatgaaaaa aatattacca tttaaaatag   4440
gcacttatta gtctttgtga tttccaccgt tactcactct atatatttaa tatcgaaata   4500
ttgaattctt ttaattttat ggtaagaatt aatcgggatt tcaataaacc ttgatttcat   4560
ttttattgaa acaccaaaat aatataatct gggttatgtg gatcataaat gcccaaacaa   4620
aaattctatt ccaaggagag taccctaatg aaatacctac tgccttctgc agccgctggg   4680
ctgttattgc ttgcggccca accaacgatg gtggcaaata cggggggtta tgccaccact   4740
gacggtggtg acgttgccgg tgccgtgaaa aaaacagcgc gctccatgca agatattatt   4800
gatatcatcg aagccgcaaa gctggattcc aatggcaaga aagtcaaagg tggcgcttta   4860
ccgcttgtca tcacctttat cggtaatgaa gacgcgctga tcaaagccgc tgaggccaac   4920
atctgcggcc agtggagtaa ggatgcccga ggtgtggaaa tcaaagagtt caccaaaggg   4980
attaccatcc ttggaactaa cggatcgtcc gccaacttcg ggatctggct gacaaagtca   5040
tccgatatcg tcatacgtaa catgcgtttt ggttacatgc cgggcggcgc gcaggatggc   5100
gatgccattc gtatcgataa cacgccgaac gtctggattg accacaacga gatcttcgcg   5160
aaaaactttg aatgcgcagg tacaaaagac ggtgacacga cattcgagtc cgcgattgat   5220
attaagaaag cttcgaccaa cgtgaccatt tcgtacaact acattcatgg catcaaaaaa   5280
gtggggctga gcggcttcag cagcagcgat acgggccgtg acctgactta tcatcacaat   5340
atttacgacg acgttaacgc tcgcctccca ctgcaacgtg gtggtcaggt tcatgcctac   5400
```

```
aacaacttgt atactggcat caccagctct ggcctgaacg tgcgtcagaa agggattgcg    5460
ctgatcgaac gtaactggtt cgagaatgcg aaaaacccag tgacctcacg ttatgacggt    5520
tccaacttcg gtacgtggga actgcgtaat aacaacgtca tgagcccagc cgacttcgct    5580
aaatacaaca tcacttggga taaagatacc aaaccctacg tgaattccga agactggaaa    5640
aacaccggta cgtttgcttc tgttccttac agctactctc cagtttctgc acagtgtgtg    5700
aaggacaaac tggcgaacta tgctggcgtg aaccaaaacc tttccgtgct gtcagcagca    5760
aattgcaact agttgcaaag cgtgaaaggt aaataagcga atagcaggcc ccgcccctca    5820
ttgtcctgtg ctaactggag cctgcaaaca agcttaacgc ccgtcggttt atcgttcggg    5880
ccgcacttga gcgagcccta agggtcgctc atttttatcg ttaatattca aggaaatgaa    5940
atgaaacgtt ctcttctgtt cgccgcactg ttcagcaccg gcttagtgta tagtgttggt    6000
ataccgatgg cgggcgccga cacaccggca gcaccagagt tgaaaggatt cggaacggat    6060
accgtagcag gcagcggtgg acgcattatt cgcgtcacca cgctagcctc ttctggagca    6120
ggttcactca gggaagcgct ggccgccaaa ggaccgcgca ttatcgtttt tgaggttggc    6180
ggcattatcg acctaaataa aagtgacctt cggttatcag aaccgtttgt caccattgcc    6240
ggccagaccg ctccctctcc cggtatcacc atcattcgcg gcggaatggg gatcagcaca    6300
catgatgtgc tgatgcagca tattcgtttc cgcatcggcg atgccggtac gggtaaaaaa    6360
agcggctttg aacgcgatgt ttccatcaac ggcaaagatg cctacaacgt cgtgatcgac    6420
cactctagtt ttcgcctggg gtacggacga aaacctgtct atttccggcc cacgctatga    6480
cggaccgcag ggcaccgcac accgcattac gctttcgaat aatatcgttg ctgaaggcct    6540
atacgattcg gctcacacca aaggtattca ctcgatgggg acgctggttc acgataacgt    6600
gaccgacgta tcgatcgtgg gcagcctgta cgcgcacaac aacgagcgta atgcctggtt    6660
taaagcaggt tctacaggtg tcatggtcaa taacctgatc tacaacccg gcatttgggg    6720 cgttcgcgtt ggtggcgtaa aaggagagtg ggaagggaaa accatgcccg ccagcccacg    6780
cgtctccgtt gcgggtaacg tgatgcacta cggcacgaat accaaagcag gtttaggact    6840
ggtaggaagc aacagctccg gcgatgtctg gatgtcagat aacctcgcgt acgatgctca    6900
gggaaaagcg gcaccgcaaa cgtcaggcag tgggattaac ttactcaaag tgtccctat    6960 ttggcctgcg ggcttaacgg catcaccggc cagcgccgtc accaatcagg tactgcaaag    7020
cgcaggcgcg cgtcctaaag gtcgtgatgc cgttgataaa cgtatcgtgg ataatttcaa    7080
acagcggaaa ggtggtttcg tgaacagcca ggaagacgtc ggcggctatc ccgttgcaac    7140
agcgacctac cgtcagctga acgtaccgag cactggcgta gatgcctggc tacagcagat    7200
ggccaacgcg ctggaataaa acggcgctca tggaatagca gagtaaaatg ctaaaaggcc    7260
acatcagtgg cctttgtcgt attctcggtt ctttgcttat ctattttgcc aatccgggca    7320
gcactttcgc ggactgaatc acgactggcg tggtcggcac attctggtaa ggcccgacat    7380
tcttcgttgg cacctgagaa atcttatcca cgacgtccat gcccttcact actttaccga    7440
acacggcgta gcccaaatca cgctggccat gatccccggg                          7480
```

<210> SEQ ID NO 6
<211> LENGTH: 374
<212> TYPE: PRT
<213> ORGANISM: Erwinia carotovora

<400> SEQUENCE: 6

Met Lys Tyr Leu Leu Pro Ser Ala Ala Ala Gly Leu Val Leu Leu Ala

```
  1               5                   10                  15
Ala Gln Pro Thr Met Ala Ala Asn Thr Gly Gly Tyr Ala Thr Thr Asp
             20                  25                  30

Gly Gly Asp Val Ser Gly Ala Val Lys Lys Thr Ala Arg Ser Leu Gln
         35                  40                  45

Glu Ile Val Asp Ile Ile Glu Ala Ala Lys Lys Asp Ser Ser Gly Lys
     50                  55                  60

Ala Val Lys Gly Gly Ala Tyr Pro Leu Val Ile Thr Tyr Asn Gly Asn
 65                  70                  75                  80

Glu Asp Ala Leu Ile Lys Ala Ala Glu Ala Asn Ile Cys Gly Gln Trp
                 85                  90                  95

Ser Lys Asp Pro Arg Gly Val Glu Ile Lys Glu Phe Thr Lys Gly Ile
             100                 105                 110

Thr Ile Leu Gly Thr Asn Gly Ser Ser Ala Asn Phe Gly Ile Trp Met
         115                 120                 125

Val Asn Ser Ser Asn Val Ile Val Arg Asn Met Arg Phe Gly Tyr Met
     130                 135                 140

Pro Gly Gly Ala Lys Asp Gly Asp Ala Ile Arg Ile Asp Asn Ser Pro
145                 150                 155                 160

Asn Val Trp Ile Asp His Asn Glu Ile Phe Ala Lys Asn Phe Glu Cys
                 165                 170                 175

Ala Gly Thr Pro Asp Asn Asp Thr Thr Phe Glu Ser Ala Val Asp Ile
             180                 185                 190

Lys Lys Ala Ser Thr Asn Val Thr Val Ser Tyr Asn Tyr Ile His Gly
         195                 200                 205

Val Lys Lys Val Gly Leu Ser Gly Ser Ser Asn Thr Asp Thr Gly Arg
     210                 215                 220

Asn Leu Thr Tyr His His Asn Ile Tyr Ser Asp Val Asn Ser Arg Leu
225                 230                 235                 240

Pro Leu Gln Arg Gly Gly Gln Val His Ala Tyr Asn Asn Leu Tyr Gly
                 245                 250                 255

Gly Ile Lys Ser Ser Gly Phe Asn Val Arg Gln Lys Gly Ile Ala Leu
             260                 265                 270

Ile Glu Ser Asn Trp Phe Glu Asn Ala Leu Asn Pro Val Thr Ala Arg
         275                 280                 285

Asn Asp Asp Ser Asn Phe Gly Thr Trp Glu Leu Arg Asn Asn Asn Ile
     290                 295                 300

Thr Ser Pro Ser Asp Phe Ala Lys Tyr Asn Ile Thr Trp Gly Lys Pro
305                 310                 315                 320

Ser Thr Pro His Ile Asn Ala Asp Asp Trp Lys Ser Thr Gly Lys Phe
                 325                 330                 335

Pro Ala Val Pro Tyr Ser Tyr Ser Pro Val Ser Ala Gln Cys Val Lys
             340                 345                 350

Asp Lys Leu Ala Ser Tyr Ala Gly Val Gly Lys Asn Gln Ala Val Leu
         355                 360                 365

Thr Ala Ala Asn Cys Lys
     370
```

USE OF PLANTS WITH REDUCED LEVELS OF DE-ESTERIFIED HOMOGALACTURONAN IN THE CELL WALL OR PORTIONS THEREOF FOR IMPROVING THE SACCHARIFICATION OF PLANT BIOMASSES

This application claims priority to and the benefit of Italian Application No. RM2008A000696 filed on Dec. 30, 2008, the content of which is incorporated herein by reference.

FIELD OF THE INVENTION

The present invention relates to a process for improving conversion of lignocellulosic biomasses into fermentable sugars, a process called saccharification, which then allows the production, on an industrial scale, of any product obtained by fermentation, including ethanol (bioethanol).

The present invention relates to the steady expression in plants of pectinolytic enzymes and of pectin methylesterase inhibitors for increasing the degradability of plant tissues through enzymatic digestion and thus the saccharification efficiency.

BACKGROUND OF THE INVENTION

The increasing demand for fuels alternative to oil derivatives is directing towards processes for production of bio fuels. The production of ethanol and biogas through the digestion process starting from complex organic matrices of a biological nature (biomasses) coming from agricultural production lines (for example residual biomasses of food or industrial crops and agro-industrial or urban waste) represents a promising way to produce renewable energy and is one of the preferred ways of disposing of organic residues and waste. A considerable portion of biomasses (about 75%) is represented by the cell walls of plants. These consist of a heterogeneous matrix composed of polymeric carbohydrates associated to other components, such as lignin and proteins. Wall polysaccharides produce simple sugars by degradation (saccharification) which can then be used by the micro organisms present in aerobic and anaerobic fermentation for the production of bioethanol and biogas, respectively. Enzymatic hydrolysis is currently regarded as the most promising technology and with the lowest environmental impact for "saccharification", that is, the conversion of raw plant material into fermentable sugars. The limiting factor in this process is the natural resistance of cell walls to enzymatic degradation. Pre-treatment technologies currently available for making biomasses sensitive to hydrolytic enzymes that degrade the single components of the plant cell wall are expensive and in some cases require, along with mechanical break-up processes, the use of toxic and/or polluting substances, such as acids, peroxides and ammonia.

The availability of more easily degradable plant material would considerably improve the use of biomasses and would reduce the need for expensive pre-treatments with a strong environmental impact. Since the accessibility of the cellulose component to the degrading enzymes is prevented by the presence of pectins, hemicelluloses and lignin, qualitative and quantitative modifications of these components in the plant walls may improve the efficiency of saccharification.

The technical problem the invention intends to solve is to decrease the recalcitrance of cell walls found in lignocellulosic biomasses to the enzymatic hydrolysis by cellulases and other degrading enzymes.

The authors have set up a process that reduces, in the cell wall of a plant, the presence of de-esterified homogalacturonan, a component of plant pectins. The reduction is achieved by expression of a hexogen polygalacturonase, for example fungal polygalacturonase (PG), and/or overexpression of a pectin methylesterases inhibitor (PMEI). The process lead to an increase in the efficacy of cellulose enzymatic hydrolysis.

The biomasses containing the pectin thus modified do not need expensive and polluting pre-treatments and allow improving the saccharification process.

PRIOR ART

Plant biomasses, that is, plants and/or parts thereof at any vegetative and desiccative state, are one of the alternative source of energy, and of renewable materials and industrial products. The plant cell walls comprise about 75% by weight of lignocellulosic biomass (1) and they can be an abundant potential source of ethanol (2-4). They consist of a heterogeneous matrix of carbohydrates polymers associated to other components, such as lignin and some proteins. The degradation of the cell wall into fermentable sugars, called saccharification, is the key process for making ethanol from such biomasses. Enzymatic hydrolysis is the most promising technology that is also compatible with the protection of the environment for saccharification (5, 6). However, such process exhibits several limits, especially for an application at industrial level, due to the recalcitrance of the cell walls to hydrolysis (7). Among the causes of such recalcitrance are: the heterogeneity and complexity of the structural components of the cell walls themselves, and the inter-polymeric interactions thereof (8); the lower efficacy of the enzymes for insoluble substrates, components of the walls (9); the presence of microbial enzyme inhibitors (10); the degree of lignification (11).

In order to make the plant biomasses accessible to cell wall degrading enzymes (CWDEs), expensive pre-treatments are currently required, which use toxic chemical products such as acids, peroxides or ammonia, often accompanied by passages of mechanical rupture. An example of pre-treatment is represented by the hydrolysis with sulphuric acid 1.3% (w/w) and autoclaving at 130° C. for 40 min (14). Such pre-treatments are in some cases inefficient, as they cause the degradation of potentially useful products that may be obtained during the biomass degradation.

It is therefore clear that the reduction or elimination of such pre-treatments would represent a significant improvement of the saccharification process (12).

To this end, the modification of the cell wall structure is a non-polluting bio-technological alternative (13).

It has been proven, for example, that the reduction in the lignin contents in the cell walls of alfalfa improves the saccharification process but reduces the plant growth (14).

In dicotyledons, particularly critical polysaccharide component for tissue integrity and accessibility to CWDEs enzymes is the cohesive pectin network that surrounds the cellulose-hemicellulose matrix, which in turn contains the main elements that impart resistance. It is also known that intermolecular pectin bonds affect wall plasticity (15-17) and that the acid form of homogalacturonan (HGA) forms cross-links with Calcium ions ($Ca^{++}$) to form "junction zones" that stiffen the cell wall (18-20). The amount of HGA, its methylation level and the distribution of methyl groups affects the formation of such "junction zones". HGA is synthesised and secreted in a highly methyl esterified form, not capable of forming the network with ions $Ca^{++}$ (21). Afterwards, it is de-esterified by pectin methylesterases (PMEs), enzymes located in the walls, which produce long chains of free carboxylic residues, capable of interacting with ions $Ca^{++}$, and thus forming the "junction zones" (22).

De-esterification of galacturonans in lignified tissues may also increase the formation of lignin-carbohydrates complex forming benzyl-ester links which could cause a further resistance of the cell wall (29).

The generation of PMEI plants and tobacco plants expressing pgaIIm (PG plants) has been described (23,24), however these documents do not mention their use in reducing resistance to saccharification of lignocellulosic biomasses.

DESCRIPTION OF THE INVENTION

The authors of the present invention have surprisingly found that the saccharification process of plant biomasses may be improved by reducing the regions of de-esterified HGA in pectin, decreasing the "glue" feature of the middle lamellas, rich in pectins, which join the cell walls of two adjacent cells.

It is therefore the object of the present invention the use of plants having a reduced content of de-esterified homogalacturonan (HGA) in the pectins of said plants cell walls and a reduced resistance to saccharification with respect to control plants in a saccharification process of plant biomasses.

Preferably, the plants are obtained by genetic transformation with a gene encoding an agent able to reduce the content of de-estherified HGA in the pectins.

Preferably, the agent is a polygalacturonase.

Still preferably the gene encoding a polygalacturonase is from *Aspergillus niger*.

Yet preferably the gene encoding a polygalacturonase is modified to produce an enzyme having a reduced specific activity.

In a preferred embodiment the gene encodes a polygalacturonase having a reduced specific activity and having the amino acid sequence of SEQ ID No. 2.

In a still preferred embodiment the gene encoding a polygalacturonase having a reduced specific activity has the nucleotide sequence of SEQ ID No. 1.

Preferably, the plants are obtained by transformation with a gene encoding an inhibitor of pectin methylesterases or with a gene encoding encoding a pectate lyase.

Still preferably, the gene encoding an inhibitor of pectin methyl esterases is of plant origin.

Yet preferably, the gene encodes an inhibitor of pectin methyl esterases having the amino acid sequence of SEQ ID No. 4.

Still preferably, the gene encoding an inhibitor of pectin methyl esterases has the nucleotide sequence of SEQ ID No. 3.

Preferably, the gene encoding encoding a pectate lyase is of bacterial origin.

Still preferably, the gene encodes a pectate lyase having the amino acid sequence of SEQ ID No. 6.

Yet preferably, the gene encoding a pectate lyase has the nucleotide sequence of SEQ ID No. 5.

In a preferred embodiment the plants are obtained by selecting natural or mutagenesis induced variants.

Plants with reduced contents of de-esterified HGA in pectins are obtainable with different methods, all comprised within the protection scope of the invention.

They are produced transgenically, transforming wild plants with a gene coding for an agent capable of reducing the contents of de-esterified HGA in pectins.

As particular embodiment, the plants are transformed with a nucleic acid of a nucleotidic sequence coding for a polygalacturonase, preferably from *Aspergillus niger*, more preferably a mutant (variant) thereof, such as to code for an enzyme with reduced specific activity; even more preferably, a mutant (variant) of the sequence of gene pgaII (GenBank ID N. XM 001397030, NT 166530), preferably deleted of the sequence from nt. 1 to nt. 81 coding for the signal peptide of 21 aa. and for the propeptide from aa. 22 to aa. 27), and with such modifications as to have a deletion of the treonin amino acid in position 34 and a replacement of the amino acidic residue asparagin 178 with an aspartate (N178D). Such positions refer to the non-mature native protein. The nucleotidic sequence coding for the mature mutated protein (pgaIIm) is as follows (SEQ ID No. 1):

```
GACAGCTGCACGTTCACCGCTGCCGCTGCTAAAGCGGGCAAGGCGAAATG
CTCTACTATCACCCTTAACAACATCGAAGTTCCAGCTGGAACCACCCTCG
ACCTGACCGGTCTCACCAGCGGTACCAAGGTCATCTTCGAGGGCACCACG
ACCTTCCAGTACGAAGAATGGGCAGGCCCCTTGATCTCCATGAGTGGCGA
ACATATCACCGTCACTGGTGCCTCCGGCCACCTCATCAATTGCGATGGTG
CGCGCTGGTGGGATGGCAAGGGAACCAGCGGAAAGAAGAAGCCCAAGTTC
TTTTACGCCCATGGCCTTGACTCCTCGTCTATTACTGGATTAAACATCAA
AAACACCCCCCTTATGGCGTTTAGTGTCCAGGCGAATGACATTACGTTTA
CCGATGTTACCATCAATAATGCGGATGGCGACACCCAGGGTGGACACGAC
ACTGATGCGTTCGATGTTGGCAACTCGGTCGGGGTGAATATCATTAAGCC
TTGGGTCCATAACCAGGATGACTGTCTTGCGGTTAACTCTGGCGAGAACA
TCTGGTTCACCGGCGGCACCTGCATTGGCGGCCACGGTCTCTCCATCGGC
TCTGTCGGCGACCGCTCCAACAACGTCGTCAAGAACGTCACCATCGAACA
CTCCACCGTGAGCAATTCCGAAAACGCCGTCCGAATTAAGACCATCTCTG
GCGCCACTGGCTCCGTGTCCGAGATTACGTACTCCAACATCGTCATGTCT
GGCATCTCCGATTACGGCCTGGTCATTCAGCAGGATTACGAAGACGGCAA
GCCTACGGGTAAGCCGACGAACGGTGTCACTATTCAGGATGTTAAGCTGG
AGAGCGTGACTGGTAGCGTGGATAGTGGGGCTACTGAGATCTATCTTCTT
TGCGGGTCTGGTAGCTGCTCGGACTGGACCTGGGACGATGTGAAAGTTAC
CGGGGGGAAGAAGTCCACCGCTTGCAAGAACTTCCCTTCGGTGGCCTCTT
GTTAG.
```

The amino acidic sequence coding the mature mutated protein (pgaIIm) is as follows (SEQ ID No. 2):

```
DSCTFTAAAA KAGKAKCSTI TLNNIEVPAG TTLDLTGLTS
GTKVIFEGTT TFQYEEWAGP LISMSGEHIT VTGASGHLIN
CDGARWWDGK GTSGKKKPKF FYAHGLDSSS ITGLNIKNTP
LMAFSVQAND ITFTDVTINN ADGDTQGGHD TDAFDVGNSV
GVNIIKPWVH NQDDCLAVNS GENIWFTGGT CIGGHGLSIG
SVGDRSNNVV KNVTIEHSTV SNSENAVRIK TISGATGSVS
EITYSNIVMS GISDYGVVIQ QDYEDGKPTG KPTNGVTIQD
VKLESVTGSV DSGATEIYLL CGSGSCSDWT WDDVKVTGGK
KSTACKNFPS VASC.
```

As an alternative example, the plants are transformed with a gene coding a pectin methylesterase inhibitor, preferably from a plant source, more preferably of sequence (Locus tag: At3g17220; NCBI n. NM_112599 and NP_188348).

The full length nucleotide sequence is as follows (SEQ ID No. 3):

ATGGCAGCAT ACCTGACGAA CAGAGTTTTA ATGTCTTCTC

TGATGTTTTT TGTAATGACT GGTTCTTTGA ACGCACAAGT

GGCAGACATA AAAGCGATAT GTGGAAAAGC GAAAAACCAA

TCCTTCTGTA CGAGCTACAT GAAATCCAAC CCAAAGACCT

CAGGTGCTGA TCTTCAAACG CTTGCAAATA TCACATTTGG

TTCTGCACAA ACAAGTGCAT CAGAAGGTTT CAGGAAAATT

CAATCTCTAG TCAAGACAGC AACCAACCCC ACTATGAAGA

AAGCATACAC CTCATGTGTA CAACATTATA AGAGTGCAAT

AAGCAGTCTC AATGATGCTA AGCAGAGCCT GGCGTCAGGC

GATGGCAAAG GGTTGAACAT TAAGGTTTCA GCAGCTATGG

AAGGACCTTC AACATGTGAA CAAGACATGG CGGATTTCAA

AGTTGATCCT TCAGCTGTGA AGAACAGTGG TGATTTTCAG

AATATTTGTG GCATTGTACT TGTCATCTCA AACATGATGT GA

The amino acid sequence coding the protein is as follows (SEQ ID No. 4):

MAAYLTNRVLMSSLMFFVMTGSLNAQVADIKAICGKAKNQSFCTSYMKSN

PKTSGADLQTLANITFGSAQTSASEGFRKIQSLVKTATNPTMKKAYTSCV

QHYKSAISSLNDAKQSLASGDGKGLNIKVSAAMEGPSTCEQDMADFKVDP

SAVKNSGDFQNICGIVLVISNMM

As a further and alternative example, *Arabidopsis* plants are transformed with a gene coding a bacterial pectate lyase from a bacterial source (pel1 pectate lyase 1 of *Pectobacterium carotovorum*) (Bartling, 1995) (NCBI n. X81847 and CAA57439) here named PL1 plants.

The full length nucleotide sequence is as follows (SEQ ID No. 5):

cccgggggat ctcaaagcaa tcgggtagcg atgctgaatc aataatgagc gaatgatagc gggtgaccgt caaggctga gctagccctg cgaaaacccc cgtttcgctg tgcgcaatct cagaggtttt cccgtgcatg acctgccgtg ctcgcaccac acgcgcgccg aacgcctgtc ccatcgcctg atggccaaga cacacgccca gaataggcag tttatcggca aagtgacgga tagcagccag tgaaatgccc gcctcatccg gcgtacaagg gccaggtgaa ttaaccaatc gctcaggggc aagccgttca atctcgcgca gcgtcagttc atcattacg ttcaccacga cctgtgcgcc aagctcgcaa aagtattggt aaaggttgta ggtaaaggag tcgtagttat cgataattag cagcatagtc -continued attgcactgt tagtcggaaa agccgtacta acatacatga aatccgcgtc aggtacccac ccctcgtcac catcaaagac aaaggtggcg atctcgctgt ttaagaaatt agcatggtaa taattttatc gatcataaat catttatttc atcagtaaac atctttatta ataggcctta tttattatcc caattcacag taaacgatta ccttgaaatt attttttaaca aaaaaaataa taagaaaaaa ccgcctatga attaattcat ttttttttaaa aggaagaaaa actaaaggga tcatttctta cgtgatattt tttggtggcg atcacaatcg ttcaacaagc gaataaccac gcatataaac gggataaaaa ataagaacc cttaaaaaca taaagacatg aatttaaatg atttaaatag aaattggttt ctatttgaaa tagatagaca caaatcctct caactgtcct ctgttattta attaatatat ttaacgcccc atcctgtatt gtttgttttt ctggtaacac ttatctcggc tttatagaca aaccttattt tcatttttgt tgaaacagcc ttttttaaatt acacagggtg tgtagtgata aatcccaaa aaattctatg tcaaggagag tacataatga aatacctact gccttctgca gcagctgggc tggtgctgct cgctgcccaa ccgacaatgg cggcaaatac gggggttat gccaccactg acggcggcga cgtttctggt gcggtgaaaa aaacggcgcg ttctctgcaa gagatcgtcg atatcattga agccgcgaaa aaggactcaa gcggtaaagc ggtcaaaggc ggagcctacc cgctcgttat tacctacaac ggtaatgaag atgcgctaat caaagccgcc gaagctaaca tctgcggcca gtggagcaaa gatccgcgcg gtgtggaaat caaagagttc accaaaggga tcaccattct cggaaccaac ggttcttccg ctaacttcgg tatctggatg gttaactctt ccaacgttat cgtacgtaac atgcgcttcg gctatatgcc gggcggtgca aaagatggtg atgccatccg tatcgataat tcaccgaacg tctggatcga ccacaacgag atcttcgcca agaacttcga atgtgccggt acgccagaca acgacaccac ctttgaatcc gcggttgata tcaagaaagc ctcaaccaac gtcaccgtgt cgtacaacta tatccatggc gtgaaaaagg tagggttgag cggttcaagc aacacggata ccggtcgtaa cctgacttac catcacaata tttacagcga tgttaactca cgtctgccgc tgcaacgtgg tggccaagtc catgcttata caacctgta tggcggcatc aaaagttcag gctttaacgt ccgtcagaaa gggatcgcac tgatcgaaag taactggttc gaaaatgcgc tcaacccagt gaccgcacgt aatgacgatt ccaacttcgg tacttgggaa ctccgtaaca acaacattac cagcccatct gattttgcta aatacaacat cacctggggt aaaccatcca caccgcacat caatgcggat

```
gactggaaga gcaccggtaa attcccagcc gtcccatata
gctactctcc agtttctgca cagtgcgtga aggataaact
ggcaagctac gctggcgtag gtaaaaacca ggcagtactg
acagcagcca actgtaaata acgcgttaa gcccgacgca
ttcgttctgc gtcgggttct tcctgagcga gtgcttcggc
ctcgctcatt tttgaaaggc cggagcaaga ttgtcagcgt
gaccgccatg aaaatagacg tcgtactcat gacaatttca
ccaataagcc gaggtctatt tttcttttat cacgtaaaga
aacgccatat agcgattaat aatcgttatt tcttaaaaaa
actaaaattc gcgataaaac tgactcatca cgcgaacaat
attgaatacg tctgtgatag tatattttga cttaaggtag
tgttttacgt tgacggcagc gatcgccaca agaaaaataa
caatttaaaa accagccaat aaagaaactc gagtgcattt
attatctact aaaaagtaa ccttatgatt taccgttact
ttaaagggaa attattttct ataaaaata aaaccatcca
atcatcagta ttaccaaatg tttcatccgc aatacattta
acatttcacc cttggactga tcttattttt tgaccacact
cccccttggtt tttcaccaaa attgaaattc attttttgttg
aaaaatttac acttgttaca tcgggcatag ggatcgataa
atgcccatga aaattctatt ccaaggagac agtgataatg
aaatacctat tgcctacggc agccgctgga ttgctattac
tcgcggctca acccgcaatg ccgcaaata cgggcggcta
tgccactacg gatggtggag aagtgtccgg tgccgtgaaa
aaaacggcac gttccatgaa agaaattgtg gatattattg
aagccgcgca agtggattca aaaggcaaga aagtcaaagg
cggtgcttac ccgctcatca tcacctatag cggtaatgaa
gactcattaa tcaaagcggc tgaaaagaat atctgcgcc
agtggagtaa agacgcacgc ggcgtacaaa tcaaagagtt
caccaaaggc attactatcc agggcaccaa tggctcatcc
gccaacttcg gtgtctggat tgtgaactct tctaatgtcg
tgctacgtaa tatccgcttt ggctatatcc cgggcggcgc
gcaacacggc gatgccattc gtatcgataa ctccccgaac
gtctggatcg accacaacga atctttgcc aagaactttg
agtgtaaagg cacgccagac aatgacacca cctttgaatc
ggctgtcgat atcaaaaaag gtcaactaa cgtcacggta
tcctacaact atattcatgg tatcaagaaa gtcggcctga
gcggcgcaag caatacggat acgggccgta acctgactta
ccatcacaat atttatagcg atgttaactc acgcctgccg
ctgcaacgtg gtggtctggt tcacgcgtac aacaacctgt
atgacggcat caccggttca ggctttaatg tgcgtcagaa
```
```
agggatcgca ctgattgaaa gcaactggtt cgagaatgcg
ctcaacccag tgacagcacg taacgacagc tcaaactttg
gtacctggga gctgcgtaac aacaacatca cgaaaccggc
agacttctcc aaaatacaaaa tcacctgggg caagccttcc
tctcctcaca tcaatgcgga tgactggaag agcaccggta
agttccctgc cgtctcctat aagtacactc cagtttctgc
acagtgcgtg aaggataaac tggcaaacta tgctggcgtc
ggtaaaaacc tggcagtact gacagcagct aactgcaaat
aaacgcggtc aggctttctc cgtcgtcgca agacaggaag
caataagtct gaatatcccg cgccgtgact cttcatacag
aagcatggtt ctacccaagc gagcctctta gagctcgctc
attttttttat ggaaactcag gcgcgaacat ggatatgcat
tcctaaagag caggcataaa ttaaatatca ggctaattat
taatataatg aattaatagc ttgatttatt aatggagaaa
accatccttt aattaatgat taatcaatag aaataacaac
agcccatcaa cacgtgatta ttaataatt tgatcggcat
caactatttc tgacgccatc atctcagcga gtaataaaac
gaaatataat tttattttttc ataaaactct caatggccta
attttagaaa aaatgaaaaa aatattacca tttaaaatag
gcacttatta gtctttgtga tttccaccgt tactcactct
atatatttaa tatcgaaata ttgaattctt ttaatttttat
ggtaagaatt aatcgggatt tcaataaacc ttgatttcat
ttttattgaa acaccaaaat aatataatct gggttatgtg
gatcataaat gcccaaacaa aaattctatt ccaaggagag
taccctaatg aaatacctac tgccttctgc agccgctggg
ctgttattgc ttgcggccca accaacgatg gtggcaaata
cggggggtta tgccaccact gacggtggtg acgttgccgg
tgccgtgaaa aaaacagcgc gctccatgca agatattatt
gatatcatcg aagccgcaaa gctggattcc aatggcaaga
aagtcaaagg tggcgcttta ccgcttgtca tcacctttat
cggtaatgaa gacgcgctga tcaaagccgc tgaggccaac
atctgcggcc agtggagtaa ggatgcccga ggtgtggaaa
tcaaagagtt caccaaaggg attaccatcc ttggaactaa
cggatcgtcc gccaacttcg ggatctggct gacaaagtca
tccgatatcg tcatacgtaa catgcgtttt ggttacatgc
cgggcggcgc gcaggatggc gatgccattc gtatcgataa
cacgccgaac gtctggattg accacaacga gatcttcgcg
aaaaactttg aatgcgcagg tacaaaagac ggtgacacga
cattcgagtc cgcgattgat attaagaaag cttcgaccaa
cgtgaccatt tcgtacaact acattcatgg catcaaaaaa
gtggggctga gcggcttcag cagcagcgat acgggccgtg
```

-continued

```
acctgactta tcatcacaat atttacgacg acgttaacgc
tcgcctccca ctgcaacgtg gtggtcaggt tcatgcctac
aacaacttgt atactggcat caccagctct ggcctgaacg
tgcgtcagaa agggattgcg ctgatcgaac gtaactggtt
cgagaatgcg aaaaacccag tgacctcacg ttatgacggt
tccaacttcg gtacgtggga actgcgtaat aacaacgtca
tgagcccagc cgacttcgct aaatacaaca tcacttggga
taaagatacc aaaccctacg tgaattccga agactggaaa
aacaccggta cgtttgcttc tgttccttac agctactctc
cagtttctgc acagtgtgtg aaggacaaac tggcgaacta
tgctggcgtg aaccaaaacc tttccgtgct gtcagcagca
aattgcaact agttgcaaag cgtgaaaggt aaataagcga
atagcaggcc ccgcccctca ttgtcctgtg ctaactggag
cctgcaaaca agcttaacgc ccgtcggttt atcgttcggg
ccgcacttga gcgagcccta agggtcgctc attttttatcg
ttaatattca aggaaatgaa atgaaacgtt ctcttctgtt
cgccgcactg ttcagcaccg gcttagtgta tagtgttggt
ataccgatgg cgggcgccga cacaccggca gcaccagagt
tgaaaggatt cggaacggat accgtagcag gcagcggtgg
acgcattatt cgcgtcacca cgctagcctc ttctggagca
ggttcactca gggaagcgct ggccgccaaa ggaccgcgca
ttatcgtttt tgaggttggc ggcattatcg acctaaataa
aagtgacctt cggttatcag aaccgtttgt caccattgcc
ggccagaccg ctccctctcc cggtatcacc atcattcgcg
gcggaatggg gatcagcaca catgatgtgc tgatgcagca
tattcgtttc cgcatcggcg atgccggtac gggtaaaaaa
agcggctttg aacgcgatgt ttccatcaac ggcaaagatg
cctacaacgt cgtgatcgac cactctagtt ttcgcctggg
gtacggacga aaacctgtct atttccggcc cacgctatga
cggaccgcag ggcaccgcac accgcattac gctttcgaat
aatatcgttg ctgaaggcct atacgattcg gctcacacca
aaggtattca ctcgatgggg acgctggttc acgataacgt
gaccgacgta tcgatcgtgg gcagcctgta cgcgcacaac
aacgagcgta atgcctggtt taaagcaggt tctacaggtg
tcatggtcaa taacctgatc tacaaccccg gcatttgggg
cgttcgcgtt ggtggcgtaa aaggagagtg ggaagggaaa
accatgcccg ccagcccacg cgtctccgtt gcgggtaacg
tgatgcacta cggcacgaat accaaagcag gtttaggact
ggtaggaagc aacagctccg gcgatgtctg gatgtcagat
aacctcgcgt acgatgctca gggaaaagcg gcaccgcaaa
```

-continued
```
cgtcaggcag tgggattaac ttactcaaag tgtcccctat
ttggcctgcg ggcttaacgg catcaccggc cagcgccgtc
accaatcagg tactgcaaag cgcaggcgcg cgtcctaaag
gtcgtgatgc cgttgataaa cgtatcgtgg ataatttcaa
acagcggaaa ggtggtttcg tgaacagcca ggaagacgtc
ggcggctatc ccgttgcaac agcgacctac cgtcagctga
acgtaccgag cactggcgta gatgcctggc tacagcagat
ggccaacgcg ctggaataaa acggcgctca tggaatagca
gagtaaaatg ctaaaaggcc acatcagtgg cctttgtcgt
attctcggtt ctttgcttat ctattttgcc aatccgggca
gcactttcgc ggactgaatc acgactggcg tggtcggcac
attctggtaa ggcccgacat tcttcgttgg cacctgagaa
atcttatcca cgacgtccat gcccttcact actttaccga
acacggcgta gcccaaatca cgctggccat gatccccggg
```

The amino acid sequence coding the protein is as follows (SEQ ID No. 6):

```
mkyllpsaaa glvllaaqpt maantggyat tdggdvsgav
kktarslqei vdiieaakkd ssgkavkgga yplvityngn
edalikaaea nicgqwskdp rgveikeftk gitilgtngs
sanfgiwmvn ssnvivrnmr fgympggakd gdairidnsp
nvwidhneif aknfecagtp dndttfesav dikkastnvt
vsynyihgvk kvglsgssnt dtgrnltyhh niysdvnsrl
plqrggqvha ynnlyggiks sqfnvrqkgi aliesnwfen
alnpvtarnd dsnfgtwelr nnnitspsdf akynitwgkp
stphinaddw kstgkfpavp ysyspvsaqc vkdklasyag
vgknqavlta anck
```

The use of plants already with reduced contents of de-esterified HGA made transgenic as described above, or double transgenic plants, is also within the scope of the invention.

The present invention shall now be described by the following figures with reference to explanatory examples non-limiting the scope of protection.

FIG. 1. Saccharification of PG (fungal polygalacturonase) and PMEI (pectin methylesterase inhibitor) plants. The efficiency of enzymatic hydrolysis, expressed as percentage of total sugars released in the medium, at the indicated times was measured in leaf tissues of non transformed (WT) and transgenic plants with cellulases (Celluclast 1.5 L) and (A), WT tobacco plants and AnPGII (*Aspergillus niger* endopolygalacturonase II, PG)) showing an enzymatic hydrolysis efficiency for PG of at least 55% at 24 hours, compared to an enzymatic hydrolysis efficiency of about 20% for WT at 24 hours; (B) *Arabidopsis* WT and expressing pgallm (PG), (C) *Arabidopsis* WT and expressing AtPMEI2 (*A. thaliana*-specific pectin methyl esterase inhibitors, PMEI); (D) Saccharification of leaf tissues of WT, PG and PMEI plants pre-treated with diluted acids before enzymatic hydrolysis. The bars represent the average ±s.e.m (n>6). The asterisks indicate statistically significant differences between WT and transgenic plants, according to the t test of Student (*, P<0.05; ***, P<0.01). The panels in the inserts demonstrate the maceration of the WT and transgenic representative samples after 48 hours of digestion.

Figure 2:
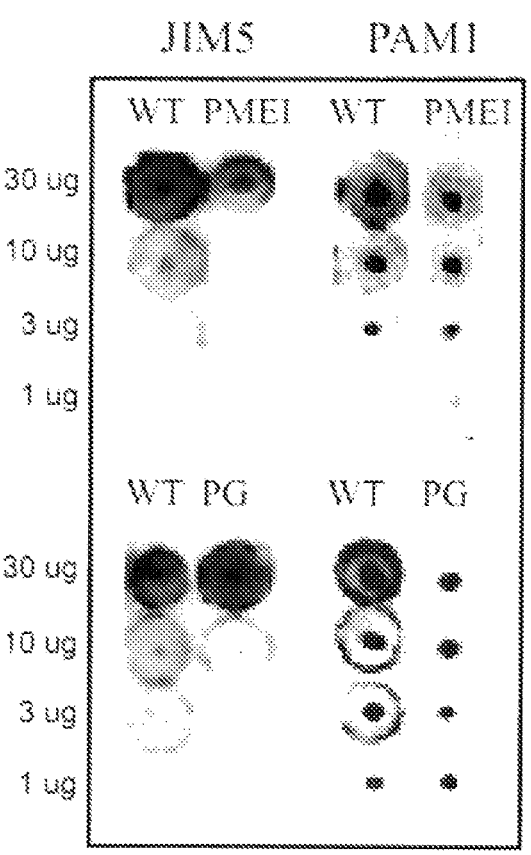

FIG. 2. Immunodot analysis of fractions of cell wall. Fractions of cell wall enriched in pectin (ChASS Chelating Agents Soluble Solids) extracted from cell wall material from leaves of WT, PMEI or AnPGII (PG) plants were applied on nitrocellulose to the dilutions indicated and tested with JIM5 and PAM1 monoclonal antibodies.

Figure 3:
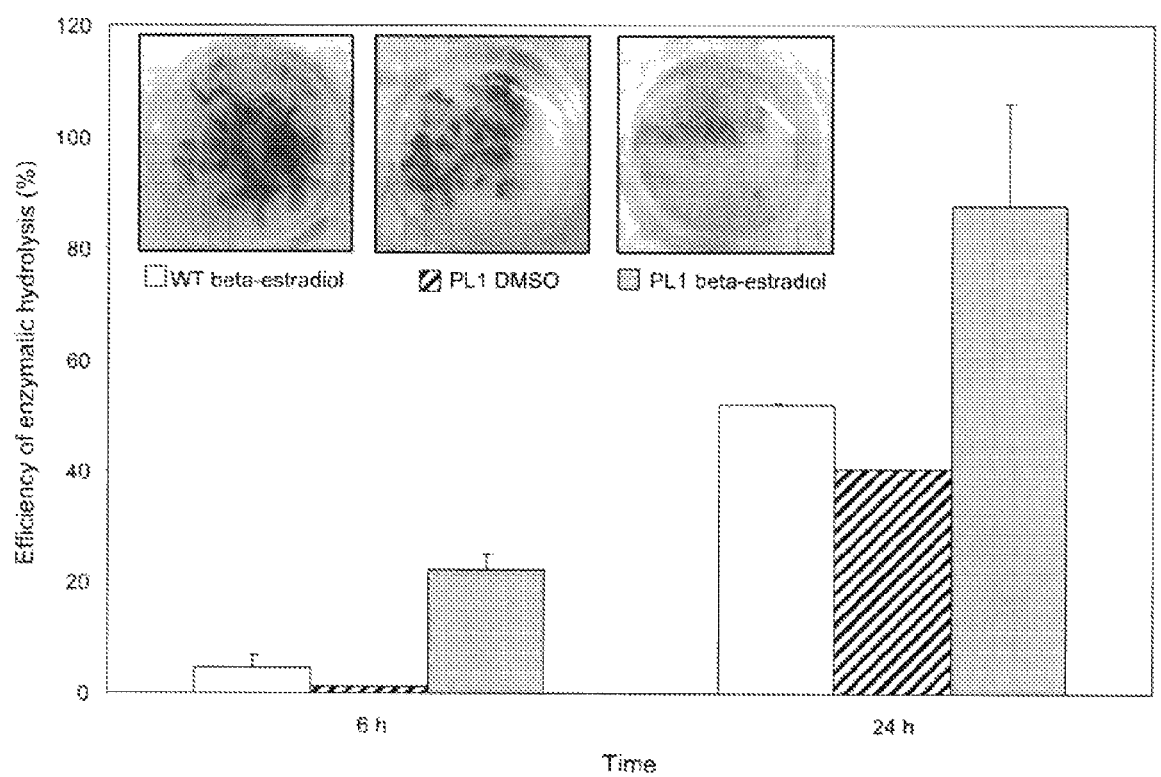

FIG. 3. Efficiency of saccharification of *Arabidopsis* WT plantules in the presence of beta-estradiol and PL1 plants with and without beta-estradiol inductor. Saccharification carried out on seedlings of non transformed (WT) and transgenic (PL1) lines with cellulose (Cellulast 1.5 L 0.1% v/v) previously treated and not treated with beta-estradiol. The efficiency of the enzymatic hydrolysis is expressed as percentage of reducing sugars released in the medium compared to the total sugars of the tissue at the times indicated. The panel in the inserts shows the maceration after 24 hours of digestion of WT seedlings incubated with 50 μM beta-estradiol, PL1 seedlings non induced and induced with beta-estradiol.

MATERIALS AND METHODS

Transgenic Plants

Plants of *Arabidopsis thaliana*, ecotype Columbia (Col.-0) were obtained from G. Redei and A. R. Kranz (Arabidopsis Information Service, Frankfurt, Germany). The generation PMEI plants and tobacco plants expressing pgallm has been described (23,24). For the transgenic expression of pgallm in *Arabidopsis*, an expression cassette was used which included the promoter of the 35S of the Cauliflower Mosaic Virus (CaMV) of the binary vector pBI121 (Stratagene: GenBank ID AF485783), the coding gene pgallm fused with peptide signal of PGIP1 from *Phaseolus vulgaris* (corresponding to the first 87 nt. of the sequence X64769 (3) and the terminator of the gene nopaline synthase (NOS) of the vector pBI121, excised from the construction described in (2) by double digestion of plasmid with PstI and EcoRI. The fragment of DNA excised was cloned in the binary vector Pcambia3300 (cambia, Can berra, Australia) and the recombinant vector used to transform the strain GV3101 (pMP90RK) of *Agrobacterium tumefaciens* through electroporation (31). *Arabidopsis* (ecotype Col-0) plants of 4 week were stably transformed with the floral-dip method (32). The transgenic plants PG or PMEI T2 plants were selected on the soil after irroration with BASTA (300 uM Phosphinothricin, PPT). The resistant lines were transferred to soil without herbicide and the seeds collected. The T2 progeny was selected on solid sterile Murashige-Skoog soil with 8 mg L$^{-1}$ of PPT, and the lines with a ratio of segregation of 3:1 by resistance to PPT were selected for analysis. The homozygous lines were analyzed for protein expression and activity by Western blot analysis and test of diffusion in agar as described in (24). The growth of WT and transformed plants was carried out in controlled environment rooms, at 22° C., 70% of relative humidity with a photoperiod of 16-h light and 8-h dark (100 μmol m$^{-2}$s$^{-1}$ of fluorescent light).

For the quantification of the fresh weight (FW) and dry weight (DW) of the rosette after 15 days of growth, the plants were transferred to a photoperiod of 12-h (100 m$^{-2}$s$^{-1}$ of fluorescent light).

The Tobacco plants were grown in a greenhouse at 23° C. and 60% relative humidity with a photoperiod of 16-h light and 8-h darkness (130 μmol m$^{-2}$s$^{-1}$ of fluorescent light).

For the transgenic expression of pel1 in *Arabidopsis*, the gene was fused to the peptide signal of PGIP1 from *Phaseolus vulgaris* (corresponding to the first 87 nt of the sequence X64769) and to the HA of the hemagglutinin of the virus of human influenza (corresponding to the 27 nt from 10 to 37 of the sequence EF014106) and was cloned in the vector of expression in plant inducible by estrogen pMDC7 (Zuo, 2000). Such vector was used to transform strain GV3101 of *Agrobacterium tumefaciens* (31) by electroporation. *Arabidopsis* (Col-0) plants of 4 week were transformed with floral-dip method (32). The T1 PL1 transgenic plants were selected after a growth of 4 days in darkness on solid soil Murashige-Skoog (MS), 0.5% sterile sucrose containing Hygromycin 20 mg/l. The plants resulting positive after selection were transferred to soil and the seeds collected. The PL1 lines selected with antibiotic were induced with 50 μM beta-estradiol and analyzed for protein expression enzymatic activity by western blot analysis using commercial antibodies against HA and enzymatic activity was detected by agar diffusion assay as described in (24) with the following modifications: the substrate was prepared by dissolving polygalacturonic acid (PGA) in 0.1M Tris-HCl pH 8 and 0.3 mM $CaCl_2$.

Enzymatic Hydrolysis

PL1 seedlings selected in solid soil containing Hygromycin were grown in light in rooms with controlled atmosphere (22° C. photoperiod 16 h light/8 h darkness 100 μmol m$^{-2}$ s$^{-1}$ of fluorescent light) for three days and afterwards 10 plants (fresh weight of approximately 200 mg) were transferred to liquid sterile culture medium MS, 0.5% sucrose. After 7 days following the transfer, the plants were transferred to sterile water containing 50 iM beta-estradiol to induce the expression of the pel1. After 24 hours of induction with beta-estradiol, the plants were treated with 0.1% cellulose (Cellulast 1.5 L) at various times as indicated in the figure at 37° C. in a solution of 50 mM buffer sodium acetate at pH5.5, sterilized through filtration. Leaf explants from WT, PG and PMEI plants (100 mg of fresh weight sterilized in a solution of 1% sodium hypochlorite for 1 minute and washed two times with sterile water to avoid microbial contamination) were incubated for 20 hours at 37° C. in a solution containing 50 mM sodium acetate buffer pH 5.5, and 0.5% Celluclast 1.5 L (cellulase from *Trichoderma reesei*; Sigma, St Louis, Mo.), already sterilized through filtration. The reducing sugars released in solution were quantified with the test PAHBAH assay (4) after centrifugation. The total sugars before enzymatic hydrolysis are determined with the Dubois (33) method.

Chemical Pre-Treatment

The leaf material was mixed with dilute sulfuric acid (final concentration 1.3%) and pre-treated at 110° C. for 20 minutes. After the pre-treatment, the hydrolyzates were separated and collected through filtration and the residual biomass washed with water.

Immunodot Assay

AIS (Insoluble solids in alcohol) were extracted as described in (23). After washing with chloroform:methanol, the material was washed twice with 80% acetone and air dried. To obtain fractions of soluble solids in chelating agents (ChASS), the AIS (approximately 10 mg) were homogenized twice in a buffer containing 50 mM TRIS-HCI and 50 mM trans-1,2-Cyclohexanediaminetetraacetic acid (CDTA) pH 7.2, at 80° C. After centrifugation at 10,000 rpm for 10 minutes, the two supernatants were united and lyophilized. Squares of 6×6 mm were marked on membranes of nitrocellulose (Amersham, UK) with a pencil and equal quantities of ChASS fractions from each line were dissolved in water and applied in the squares drawn on the nitrocellulose, respectively in dilutions of about 3×. Specific peptic epitopes were revealed with the monoclonal antibodies PAM1 (25, 26) and JIM5 (26) (provided by Prof. P. Knox University of Leeds).

The membranes were blocked in MPBS (1×PBS with 3% "Membrane blocking reagent powder", Amersham, UK) for 1 hour before the incubation with the primary ab (supernatants of hybridomas of JIM5 and LM7 diluted 1/10 or of PAM1 diluted 1/20 in 3% MPBS) for 1.5 h. After washing in 1×PBS, the membranes were incubated with the secondary ab (anti-rat conjugate with peroxidase from radish, Amersham, UK) diluted 1/1000 for JIM5 and with an anti-histidine antibody conjugate with peroxidase from radish (Sigma A-7058) diluted 1/1000 for PAM1. The membranes were washed as described and subsequently treated with the ECL reagent (Amersham, UK) for the measurement of the peroxidase activity.

Results

The authors analyzed the efficiency of saccharification from leaf tissues of transgenic plants expressing a polygalacturonase from *Aspergillus niger* (PG plants) and of plants overexpressing an inhibitor of the PME (PMEI plants) (24).

The PG plants show reduced levels of HGA, while the PMEI plants have a reduced activity of PME and an increased methylation of HGA.

In PG plants of *Arabidopsis* or tobacco (FIGS. 1A and B) and PMEI plants of *Arabidopsis* (FIG. 1C), the treatment of leaf tissues with commercial cellulase (Celluclast 1.5 L) for 24 hours causes a release of higher amount of sugars than in control WT plants.

The saccharification of PG and PMEI plants is accompanied by an increased maceration of the tissues (see inserts in the FIG. 1A-C). After an incubation of 24 hours without cellulase no release or sugars or maceration of the tissues was noted in both transformed and WT plants. This proves that the reduction in the HGA content or in its methylation does not cause by itself the disassembling of the tissues and the saccharification, but rather promotes the capacity of the cellulases to degrade the cellulose in the intact tissue. Furthermore, the efficiency of enzymatic hydrolysis on acid pre-treated leaves from WT transgenic (PG and PMEI) plants does not differ significantly (FIG. 1D). It must be noted that, after 24 hours of saccharification, the efficiency of enzymatic hydrolysis obtained with acid pre-treated leaves of all the plants is the same as that observed with the transgenic plants not pre-treated. No significant release of sugars is obtained after acid pre-treatment alone, regardless of the plants used. The results indicated that the degradability of the cellulose is improved in tissues from PG and PMEI plants and that it is not necessary to pre-treat such plants with acid to obtain a good saccharification.

A possible explanation is the reduced content of "junction zones" due to the particular HGA characteristics in these plants.

PG plants from tobacco have been described to show a reduced content of galacturonic acid (GalA) (23), which reduces the possibility that long chains of HGA are formed, which are necessary for the formation of "junction zones". On the other hand, even if the PMEI plants have the same content of GalA as the WT, they show an increased level of pectin methylation (24) which also prevents the formation of "junction zones".

To verify the presence of de-esterified regions of HGA in PG and PMEI plants compared to the WT ones, the following are used: a monoclonal antibody PAM 1, which specifically recognizes large de-esterified blocks of HGA (at least 30 continuous units of GalA) (25, 26) and a monoclonal antibody JIM5, which binds to pectin of low methylation level (level of methylesterification up to 40%) (26). Serial dilutions of pectic polysaccharides enriched in polyuronides (chelating agents solid solubles, ChASS), extracted from leaves of WT or *Arabidopsis* transgenic plants as in Lionetti et al. (Lionetti, V. et al. 2007). The PAM1 antibody binds epitopes both in PG and PMEI plants, but to a lesser extent than in WT plants, indicating that both the transformed plants show a reduced quantity of de-methylated HGA.

The JIM5 also binds epitopes in PG and PMEI plants, but to a lesser extent than in WT plants (FIG. 2), indicating the presence of HGA with a higher degree of methylesterification.

In conclusion, the authors have demonstrated that the reduction of de-esterified HGA in cell walls increase the efficiency of enzymatic hydrolysis in the plant tissues. This change is advantageously used to improve the process of saccharification used in the production of bio fuels and other bio-products.

The reduction of de-esterified HGA in the cell walls of plant tissues can be obtained in different ways, such as genetic transformation for the obtention of PG and/or PMEI transgenic plants; selection of natural or mutagenesis-induced variants having elevated levels of endogenous PMEI or lower level of PME.

The PMEI plants have a better saccharification and also an increased yield of biomass production (approximately 80% increase) (Table I) (17, 24, 28).

TABLE 1

Fresh weight (FW) and dry weight (DW) of the rosette of WT, PG and PMEI *Arabidopsis* plants.

| Line | Rosette FW (mg) | DW/FW ratio (%) |
| --- | --- | --- |
| WT | 137.9 ± 10 | 11.4 ± 1.8 |
| PG | 81.6 ± 2.9 *** | 9.9 ± 1.9 |
| AtPMEI | 253.4 ± 18.3 *** | 11.2 ± 0.2 |

The data represents the average ± s.e.m. of at least 6 independent samples. The asterisks indicate significant differences compared to WT according to the t test of Student ($P < 0.001$).

Moreover, the plants of the invention, in particular PMEI plants display an increased resistance to microbial pathogens (24) and are therefore an ideal source of biofuels and of other commercial products.

BIBLIOGRAPHIC REFERENCES

1. Poorter, H. & Villar, R. in Plant resource allocation. eds. Bazzaz F A & Grace J. 39-72 (Academic Press, San Diego, USA; 1997).
2. Himmel, M. E. et al Science 315, 804-807 (2007).
3. Sanders, J., et al., Macromol. Biosci. 7, 105-117 (2007).
4. Willke, T. & Vorlop, K. D. Appl. Microbiol. Biotechnol. 66, 131-142 (2004).
5. Ogier J C, et al., J Oil Gas Sci Technol 54, 67-94 (1999).
6. Yu, Z. & Zhang, H. Bioresour. Technol 93, 199-204 (2004).
7. Himmel, M. E. et al Science 315, 804-807 (2007).
8. Iiyama, K., Lam, T., & Stone, B. A. Plant Physiol 104, 315-320 (1994).
9. Himmel, M. E. et al Science 315, 804-807 (2007).
10. Klinke, H. B., et al., Appl. Microbiol. Biotechnol. 66, 10-26 (2004).
11. Cosgrove, D. J. Nat. Rev. Mol. Cell Biol. 6, 850-861 (2005).

12. Lynd, L. R. et al Nat. Biotechnol. 26, 169-172 (2008).
13. Carpita, N. C. & McCann, M. C. in Biochemistry and Molecular Biology of Plants. eds. Buchanan, B. B., Gruissem, W., & Jones, R. 52-109 (American Society Plant Physiologists, Rockville, Md.; 2000).
14. Chen, F. & Dixon, R. A. Nat. Biotechnol. 25, 759-761 (2007).
15. Ezaki, N., et al., Plant and Cell Physiology 46, 1831-1838 (2005).
16. Proseus, T. E. & Boyer, J. S. Ann. Bot. 98, 93-105 (2006).
17. Derbyshire, P., McCann, M. C., & Roberts, K. Bmc Plant Biology 7, (2007).
18. Ridley, B. L., O'Neill, M. A., & Mohnen, D. Phytochemistry 57, 929-967 (2001).
19. Voragen, A. G. J., et al., G. C. in Food polysaccharides and their applications. ed. Stephen, A. M. 287-339 (Marcel Dekker Inc., New York; 1995).
20. Brown, J. A. & Fry, S. C. Plant Physiol. 103, 993-999 (1993).
21. Zhang, G. F. & Staehelin, L. A. Plant Physiol. 99, 1070-1083 (1992).
22. Pelloux, J., Rusterucci, C., & Mellerowicz, E. J. Trends Plant Sci. 12, 267-277 (2007).
23. Capodicasa, C. et al Plant Physiol 135, 1294-1304 (2004).
24. Lionetti, V. et al Plant Physiol 143, 1871-1880 (2007).
25. Willats, W. G., Gilmartin, P. M., Mikkelsen, J. D., & Knox, J. P. Plant J 18, 57-65 (1999).
26. Willats, W. G. et al Carbohydr. Res. 327, 309-320 (2000).
27. Willats, W. G. T. & Knox, J. P. Anal. Biochem. 268, 143-146 (1999).
28. Hasunuma, T., Fukusaki, E., & Kobayashi, A. J. Biotechnol. 111, 241-251 (2004).
29. Grabber, J. H. and Hatfield, R. D. (2005b) J. of Agricult. and Food Chem. 53:1546-1549.
30. Toubart, P., et al., (1992). Plant J. 2:367-373.
31. Koncz, C. and Schell, J. (1986). Mol. Gen. Genet. 204: 383-396.
32. Clough, S. J. and Bent, A. F. (1998). Plant J 16:735-43.
33. Dubois M, et al., (1956). Anal. Chem. 28, 350-356.
34. Bartling S, Wegener C, Olsen O. Microbiology (1995), 141, 873-881
35. Zuo J, Niu Q-W, Chua N-H The plant Journal (2000) 24(2), 265-273Zuo J, Niu Q-W, Chua N-H The plant Journal (2000) 24(2), 265-273

The invention claimed is:

1. A method of producing sugars from plant biomass, the method comprising enzymatically hydrolyzing biomass of transgenic plants having a reduced content of de-esterified homogalacturonan (HGA) in the pectins of said plants cell walls and a reduced resistance to saccharification with respect to control plants, wherein said transgenic plants are obtained by transformation with a gene encoding an inhibitor of pectin methyl esterases, wherein the inhibitor of pectin methyl esterases has the amino acid sequence of SEQ ID NO: 4.

2. The method according to claim 1 wherein the gene encoding an inhibitor of pectin methyl esterases has the nucleotide sequence of SEQ ID NO: 3.

3. The method of claim 1 wherein the reduced resistance to saccharification with respect to control plants provides an enzymatic hydrolyzation efficiency expressed as percentage of total sugars released, of at least 55%, compared to an enzymatic hydrolysis efficiency of about 20% for plant biomass from non transformed plants, at 24 hours.

4. The method of claim 1 further comprising a step of pretreating the biomass of transgenic plants with a dilute acid.

* * * * *